United States Patent [19]

Kawada

[11] Patent Number: 4,490,113
[45] Date of Patent: Dec. 25, 1984

[54] DENTAL HANDPIECE

[75] Inventor: Shosaku Kawada, Kanuma, Japan

[73] Assignee: Nakanishi Dental Mfg. Co., Ltd., Kanuma, Japan

[21] Appl. No.: 574,022

[22] Filed: Jan. 26, 1984

[51] Int. Cl.³ ............................................. A61C 1/02
[52] U.S. Cl. .................................... 433/104; 433/126
[58] Field of Search ..................... 433/104, 126, 132

[56] References Cited

U.S. PATENT DOCUMENTS

| 4,075,761 | 2/1978 | Behne et al. | 433/126 |
| 4,148,143 | 4/1979 | Fleer | 433/132 |
| 4,182,038 | 1/1980 | Fleer | 433/126 |
| 4,218,216 | 8/1980 | Sugai et al. | 433/104 |

Primary Examiner—John J. Wilson
Attorney, Agent, or Firm—Wenderoth, Lind & Ponack

[57] ABSTRACT

A dental handpiece has a powerhead assembly connected to a hollow handle portion including a tube supplying air under pressure, a water tube and an exhaust tube, a holding sleeve held to the hollow handle portion and a rotatably and detachable connecting means. The tube supplying air under pressure is connected through an interconnecting tube to a flexible air tube, the water tube is connected to a flexible water tube and the exhaust tube is connected to a flexible exhaust tube respectively while permitting the holding sleeve and the connecting means to rotate relative to each other about the longitudinal axis of the handpiece with a limited angle.

4 Claims, 8 Drawing Figures

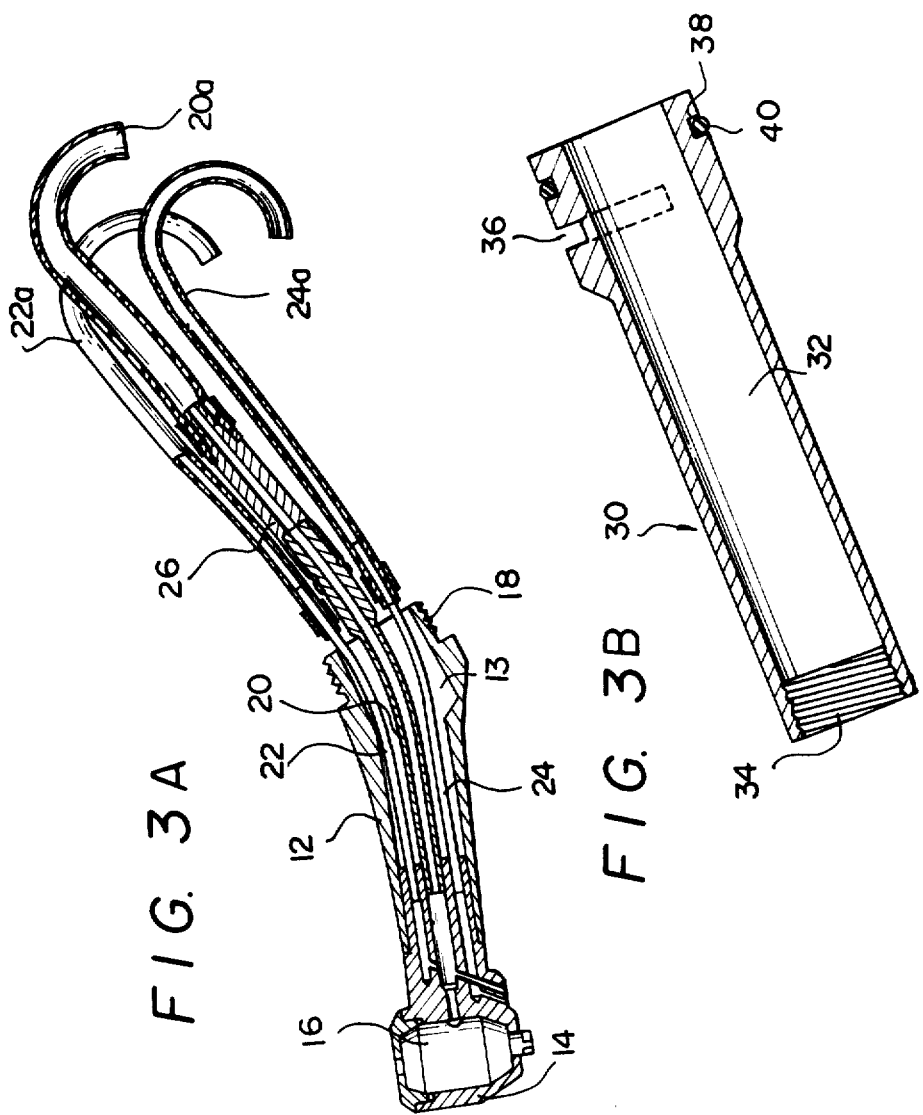

4,490,113

DENTAL HANDPIECE

BACKGROUND OF THE INVENTION

This invention relates to improvements to a dental handpiece, and more particularly to a dental handpiece having a holding sleeve including flexible tubes and a connecting means rotatably and detachably held to the holding sleeve.

In the conventional dental handpiece such as disclosed in the specifications of the Japanese Patent Application Publication (not-examined) No. 56,292/1979 and the Japanese Utility Model Application Publication (not-examined) No. 109,709/1981, a dental handpiece having a holding sleeve and a connecting means rotatably and detachably connected to each other has been proposed, but its construction is complicated and leakage of air under pressure and water can not be completely avoided.

SUMMARY AND OBJECTS OF THE INVENTION

A principal object of this invention is to provide a dental handpiece having a hollow handle portion, a holding sleeve including three flexible tubes and a connecting means whereby the holding sleeve and the connecting means are rotatable relative to each other within a limited angle around the axis of the dental handpiece.

Another object of this invention is to provide a dental handpiece having a hollow handle portion including a tube for supplying air under pressure, a water tube and an exhaust tube, and an interconnecting tube rotatably interconnecting the tube for supplying air under pressure with the flexible air tube extending through the holding sleeve to obtain the limited relative rotation between the holding sleeve and the connecting means.

Another object of this invention is to provide a dental handpiece comprising a hollow handle portion, a pneumatic motor mounted at one end of a powerhead assembly to drive a dental tool, a holding sleeve, and a connecting means releasably and relatively rotatably connected to the rear end of the holding sleeve whereby the holding sleeve and the connecting means can be either removed from the hollow handle portion or connected to the hollow handle portion quite easily and quickly.

Another object of this invention is to provide a dental handpiece whereby leakage of compressed air and water can be entirely avoided.

Another object of this invention is to provide a dental handpiece comprising a connecting means and a mount insert, each including a radial oiling filler, and a filler cap whereby oiling can be easily carried out.

Another object of this invention is to provide a dental handpiece whereby the affected part can be treated easily by limitedly rotating the connecting means with the holding sleeve.

Another object of this invention is to provide a dental handpiece which can be easily and quickly maintained by performing repairs.

Another object of this invention is to provide a dental handpiece which can be driven smoothly and quietly.

Still another object of this invention is to provide a dental handpiece which is comparatively simple and small, light in weight and at the same time desirably rigid, strong and durable.

BRIEF DESCRIPTION OF DRAWINGS

The above and further objects and novel features of the invention will more fully appear from the following detailed description when the same is read in connection with the accompanying drawings. It is to be expressly understood, however, that the drawings are for purpose of illustration only and are not intended as a definition of the limits of the invention.

FIG. 3A is an enlarged vertical sectional view of the hollow handle portion;

FIG. 3B is an enlarged vertical sectional view of the holding sleeve;

FIG. 4 is an enlarged transverse sectional view on line line IV—IV of FIG. 2;

FIG. 5 is a similar transverse sectional view of FIG. 2, with the connecting means peripherally rotated around the holding sleeve.

DETAILED DESCRIPTION OF THE PREFERRED EMBODIMENT

Figure 1:
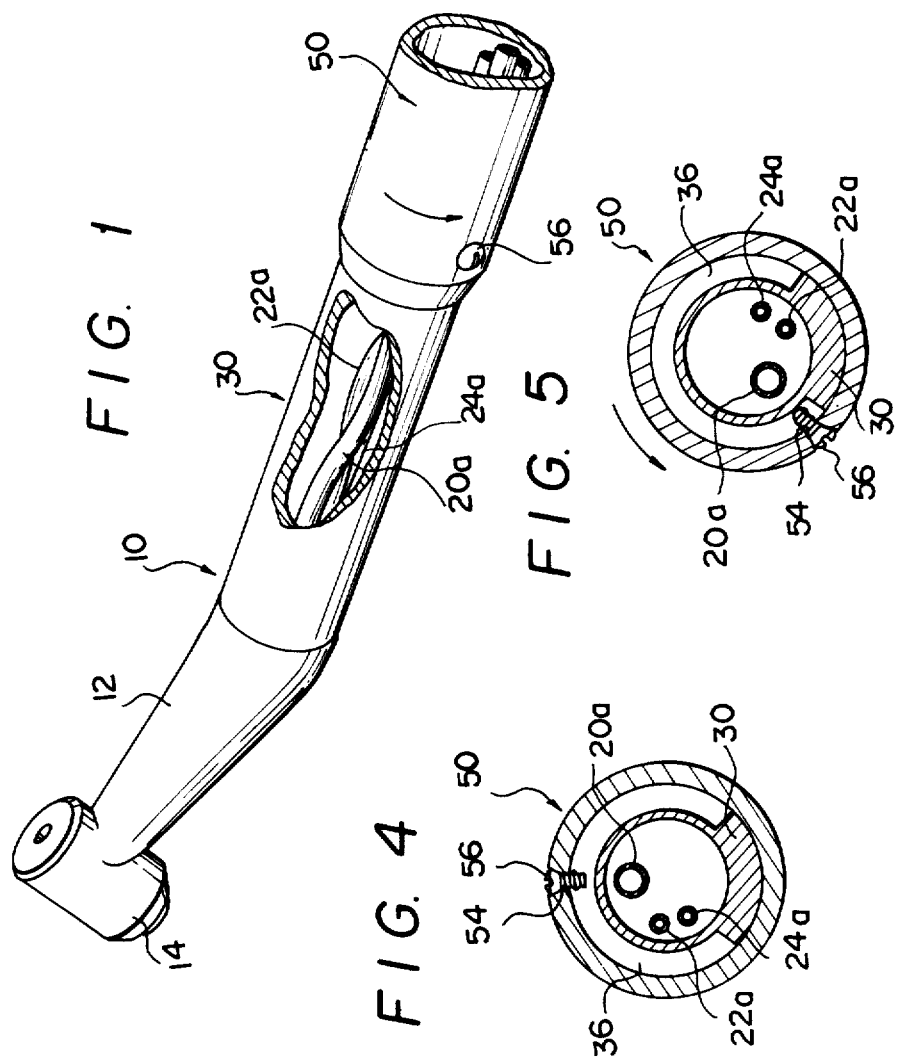
FIG. 1 is a partially cut away perspective view of a preferred embodiment of a dental handpiece according to the invention.
Figure 2:
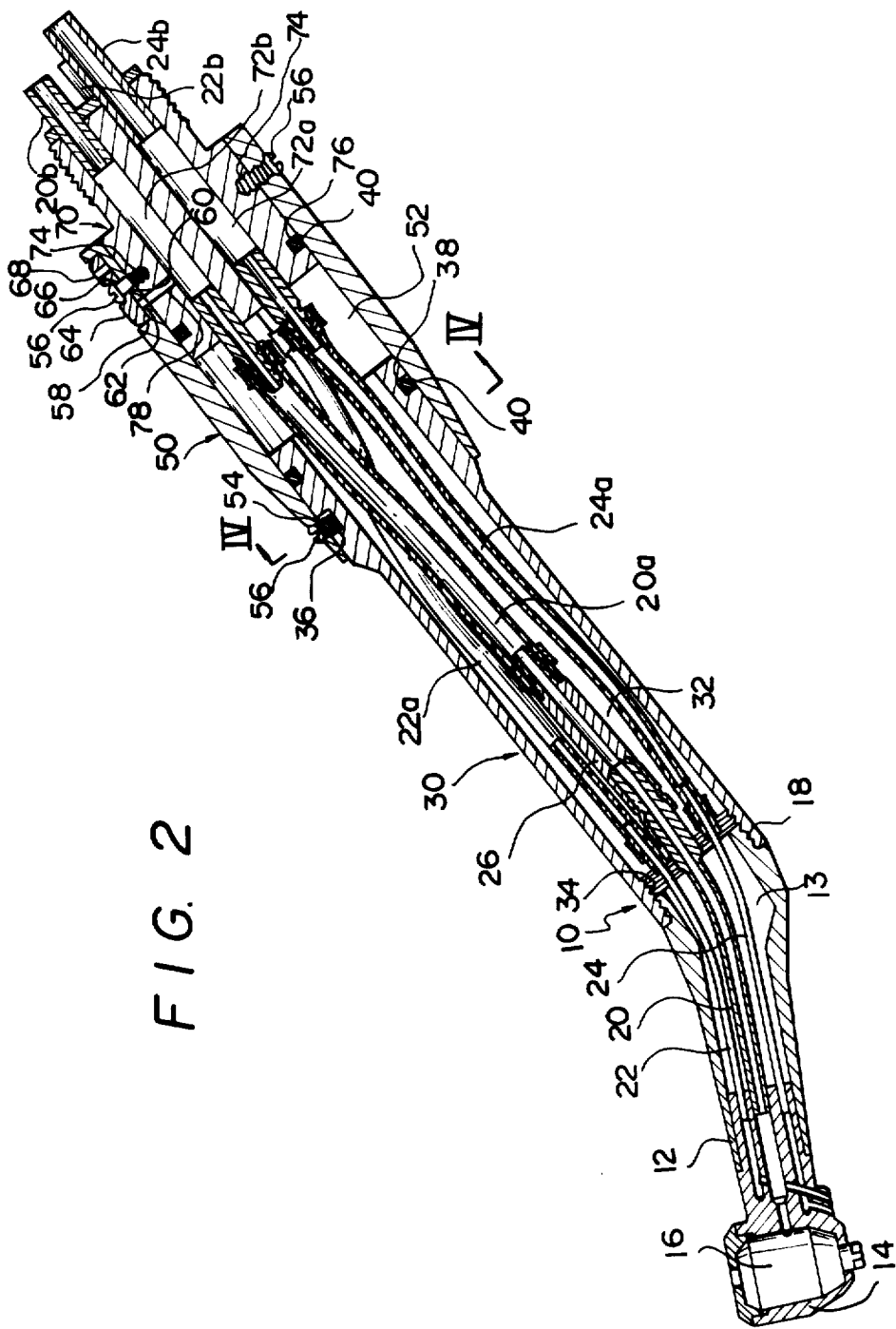
FIG. 2 is a greatly enlarged vertical sectional view of the dental handpiece shown in FIG. 1.
Figure 3C:
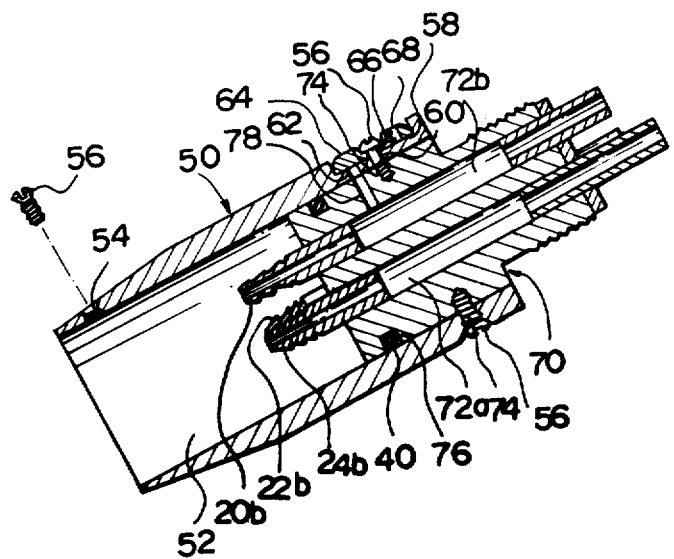
FIG. 3C is an enlarged vertical sectional view of the connecting means.
Figure 6:
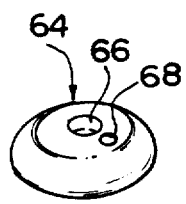
FIG. 6 is a perspective view of a cap for a oiling filler.

Referring to the drawings, the dental handpiece 10 of this invention comprises a hollow handle portion 12 and a powerhead assembly 14 which is integrally supported on a front end of the handle portion. At the top end of the powerhead assembly 14 is a pneumatic motor 16 which operates, when energized, to rotate at high speed a dental tool (not shown), and external screw threads 18 are provided around the rear periphery of the handle portion 12.

A tube 20 for supplying air under pressure is centrally and axially provided to extend through a substantial length of of the hollow handle portion 12, and a water tube 22 and an exhaust tube 24 are also axially provided near and around the air tube 20, the rear ends of these tubes extending into a central hollow portion 32 of a holding sleeve 30 when it is held to the handle portion 12.

Air-tightly and rotatably connected to the rear end of the air tube 20 is an interconnecting tube 26. A flexible air tube 20 has a front end fixedly connected to the interconnecting tube 26 and a rear end fixedly extending into a tube 20b extending through a mount insert 70. A flexible water tube 22a has a front end fixedly connected to the rear end of the water tube 22 and a rear end connected to a front end of a water tube 22b penetrating the mount insert 70. A flexible exhaust tube 24a has a front end fixedly joined into a tube 24b extending through the mount insert 70.

The holding sleeve 30 includes internal screw threads 34 which are threadedly secured on the external screw threads 18 of the handle portion 12, and a guide slot 36 is circumferentially provided around the rear end of the holding sleeve 30 to extend almost its periphery but less than 360°. A circumferential slot 38 is also provided near the rear 3nd of the sleeve for receiving a seal ring 40.

A connecting means 50 having a threaded radial opening 54 near its front periphery is also provided with a circular recess 58 at a peripheral end portion thereof, threaded openings 60 are diametrically provided in the circular recess 58 and on its opposite side, and a radial oiling filler 62 is provided in the circular recess and near the threaded opening 60 to extend into an axial hollow opening 72b thereof.

A filler cap 64 having a central opening 66 is also provided with an oiling filler 68 at a position to coincide with the radial oiling filler 64 of the connecting means 50.

The mount insert 70 having three axial and parallel openings 72a, 72b and 72c (not shown) is provided with diametrical threaded openings 74 to coincide with the two threaded openings 60 of the connecting means 50.

Recessed inwardly from the cylindrical wall of the mount insert 70 is a circumferential slot 76, into which a seal ring 40 is fitted.

The tube 20b supplies air under pressure and extends through the opening 72a. The tube 22b provided water and extends through the opening 72b. The exhaust tube 24b extends through the opening 72c.

The tubes 20a, 22a and 24a axially penetrate the hollow portion 32 of the holding sleeve 30 and extend into the hollow portion 52 of the connecting means 50.

The connecting means 50 is releasably and relatively rotatably connected to the rear end of the holding sleeve 30 to locate the threaded radial opening 54 at the radial opening 36 of the latter, and a set screw 56 is screwed through the threaded radial opening 54 to extend into the radial opening 36.

The mount insert 70 is fixedly inserted into the hollow portion 52 of the connecting means 50 so that the rear end of the air tube 20a is connected to a front end of the air tube 20b, the rear end of the water tube 22a is connected to a front end of the water tube 22b and the rear end of the exhaust tube 24a is connected to a front end of the exhaust tube 24b respectively.

Inserted into the circular recess 58 is the filler cap 64, which is rotatably held by the set screw 56 threadedly inserted through the radial openings 66 and 74 on the opposite side of the filler cap 64.

A radial oiling filler 78 is also provided through the mount insert 70 at a position to coincide with the radial oiling filler 62 of the connecting means 50 so that when the filler cap 64 inserted into the circular recess 58 is rotatably adjusted to fit its radial oiling filler 62 to the radial oiling filler 78 of the mount insert, oiling into the connecting means 50 can be easily carried out.

From the foregoing, it is believed that the features and advantages of my invention will be readily apparent to those skilled in the art and it will be understood that changes in the form, proportion and minor details of construction may be resorted to without departing from the spirit or scope of the appended claims.

I claim:

1. A dental handpiece for connection to a dental unit comprising:
   a hollow handle portion;
   a powerhead assembly integrally supported on a front end of said hollow handle portion;
   said hollow handle portion including a tube for supplying air under pressure centrally and axially provided to extend through a substantial length of said hollow handle portion, a water tube and exhaust tube also axially provided near and around said air tube, the rear ends of these tubes extending partially out of said hollow handle portion;
   a holding sleeve fixedly held in said hollow handle, said holding sleeve having a guide slot circumferentially provided around the rear end portion of said sleeve to extend almost its periphery but less than 360°;
   an interconnecting tube having its front end fixedly connected to a rear end of said tube for supplying air under pressure and its rear end air-tightly and rotatably connected to a front end of a flexible air tube extending through said holding sleeve;
   a flexible water tube having its front end fixedly connected to a rear end of said water tube extending through said hollow handle portion;
   a flexible exhaust tube having its front end connected to a rear end of said exhaust tube;
   a connecting means rotatably and releasably connected to a rear end of said holding sleeve, said connecting means having a threaded radial opening near its front periphery, a circular recess provided at a peripheral end portion thereof, threaded openings diametrically provided in said circular recess and on its opposite side, and a radial oiling filler provided in the circular recess and near the threaded opening;
   a set screw held through the threaded radial opening of said connecting means and radially extending into the guide slot of said holding sleeve;
   a filler cap rotatably fitted into said circular recess and held by a set screw and having a central opening to coincide with the radial oiling filler of said connecting means;
   a mount insert fixedly inserted into a rear end interior of said connecting means, said mount insert having three axial and parallel openings, diametrically threaded openings provided to coincide with two threaded openings of said connecting means, and a radial oiling filler provided to coincide with the radial oiling filler of said filler cap;
   a first tube extending through said first opening of said mount insert and having its front end connected to a rear end of said flexible air tube;
   a second tube extending through said second opening of said mount insert and having its front end connected to a rear end of said flexible water tube; and
   a third tube extending through said third opening of said mount insert and having its front end connected to a rear end of said flexible exhaust tube.

2. A dental handpiece as in claim 1, wherein the set screw held through the threaded radial opening of the connecting means is partially protruded into the guide slot of said holding sleeve in order to obtain the limited free rotation between the connecting means and the holding sleeve.

3. A dental handpiece as in claim 1, wherein the tube for supplying air under pressure is connected through the interconnecting tube to the flexible air tube extending through said holding sleeve, the water tube is connected to the flexible water tube, and the exhaust tube is connected to the flexible exhaust tube so that the limited free rotation between the connecting means and the holding sleeve is obtained by resiliency of these flexible tube.

4. A dental handpiece as in claim 1, wherein the filler cap inserted into the circular recess of the connecting means is rotatably adjusted to fit the radial oiling filler of said filler cap to those of the connecting means and the insert mount so as to enable oiling into said insert mount.

* * * * *